(12) United States Patent
Kim et al.

(10) Patent No.: US 8,731,631 B2
(45) Date of Patent: *May 20, 2014

(54) SYSTEMS AND METHODS FOR MAKING AND USING MEDICAL ABLATION SYSTEMS HAVING MAPPING CATHETERS WITH IMPROVED ANCHORING ABILITY

(71) Applicant: Boston Scientific Scimed, Inc., Maple Grove, MN (US)

(72) Inventors: Isaac Kim, San Jose, CA (US); Josef V. Koblish, Sunnyvale, CA (US); David McGee, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/770,847

(22) Filed: Feb. 19, 2013

(65) Prior Publication Data
US 2013/0165759 A1   Jun. 27, 2013

Related U.S. Application Data

(63) Continuation of application No. 12/854,692, filed on Aug. 11, 2010, now Pat. No. 8,380,275.

(60) Provisional application No. 61/233,965, filed on Aug. 14, 2009.

(51) Int. Cl.
  *A61B 5/042* (2006.01)
  *A61B 18/02* (2006.01)
  *A61B 18/14* (2006.01)

(52) U.S. Cl.
  USPC ............... 600/374; 600/381; 606/21; 606/41

(58) Field of Classification Search
  USPC ............................. 600/374, 381; 606/21, 41
  See application file for complete search history.

(56) References Cited

U.S. PATENT DOCUMENTS

| | | | |
|---|---|---|---|
| 5,242,441 | A | 9/1993 | Avitall |
| 2001/0039413 | A1 | 11/2001 | Bowe |
| 2002/0177765 | A1 | 11/2002 | Bowe |
| 2004/0167509 | A1 | 8/2004 | Taimisto |
| 2005/0010095 | A1 | 1/2005 | Stewart et al. |
| 2005/0267463 | A1 | 12/2005 | Vanney |
| 2006/0241366 | A1 | 10/2006 | Falwell et al. |
| 2007/0250040 | A1 | 10/2007 | Provost et al. |
| 2008/0249518 | A1 | 10/2008 | Warnking et al. |
| 2010/0057074 | A1 | 3/2010 | Roman et al. |

FOREIGN PATENT DOCUMENTS

| | | | |
|---|---|---|---|
| WO | 0137925 A2 | 5/2001 | |
| WO | 0137925 A3 | 12/2001 | |

*Primary Examiner* — Lee S Cohen
(74) *Attorney, Agent, or Firm* — Seager, Tufte & Wickhem, LLC

(57) ABSTRACT

A mapping catheter includes an elongated body for inserting into patient vasculature. A distal end of the elongated body includes a distal portion that includes a plurality of electrodes, a proximal portion disposed proximal to the distal portion, and a reduced-dimension portion disposed between the proximal and distal portions. The distal end is formed, at least in part, from a memory shape material that bends into a preformed shape upon release from a confined space. The preformed shape includes a first loop formed, at least in part, by the distal portion. The first loop is transverse to a longitudinal axis of the proximal portion. The reduced-dimension portion is configured and arranged to bend such that the reduced-dimension section advances distally through the first loop when the first loop is held in a fixed position and a force is applied distally along the longitudinal axis of the proximal portion.

20 Claims, 16 Drawing Sheets

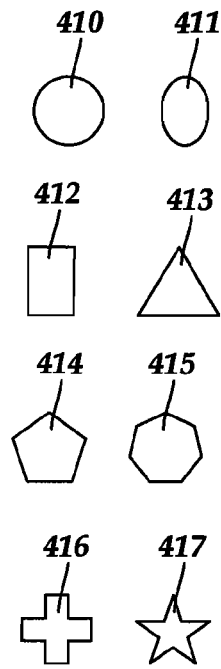
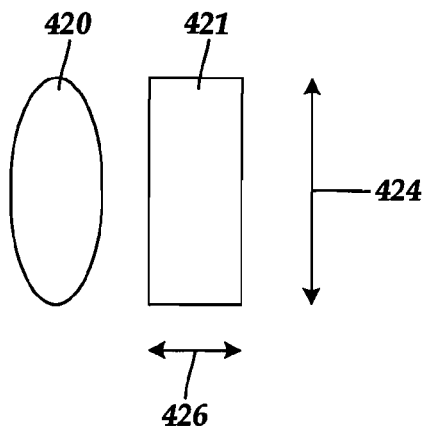
Fig. 4D
Fig. 4C
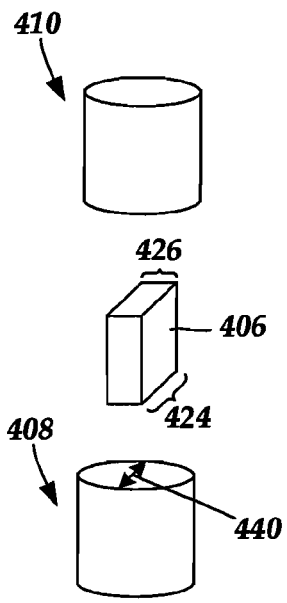
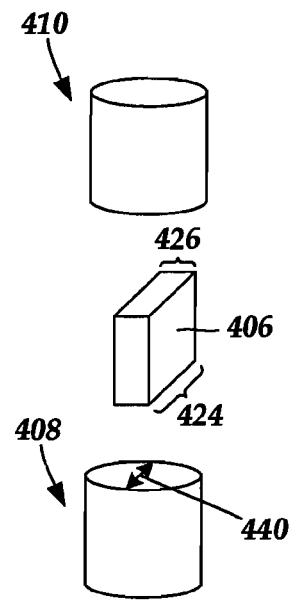
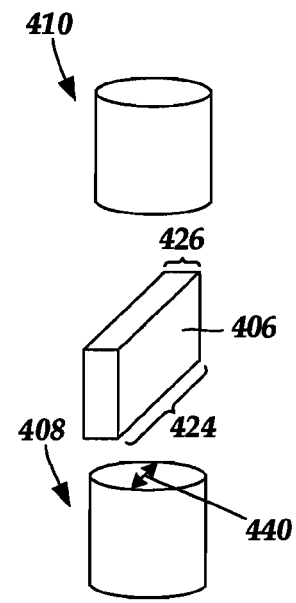
Fig. 4E  Fig. 4F  Fig. 4G

SYSTEMS AND METHODS FOR MAKING AND USING MEDICAL ABLATION SYSTEMS HAVING MAPPING CATHETERS WITH IMPROVED ANCHORING ABILITY

CROSS-REFERENCE TO RELATED APPLICATIONS

This application is a continuation of U.S. patent application Ser. No. 12/854,692 filed Aug. 11, 2010, now U.S. Pat. No. 8,380,275; which claims the benefit of priority to U.S. Provisional Application No. 61/233,965, filed Aug. 14, 2009, the entire disclosures of which are hereby incorporated by reference.

TECHNICAL FIELD

The present invention is directed to the area of medical ablation systems and methods of making and using the medical ablation systems. The present invention is also directed to medical ablation systems having mapping catheters configured and arranged for facilitating the anchoring ability of the mapping catheters to patient tissue, as well as systems and methods for making and using the medical ablation systems and mapping catheters.

BACKGROUND

Medical ablation systems (e.g., cryoablation systems, radio-frequency ablation systems, or the like) have proven therapeutic. Cryoablation systems can be used to form cold-induced lesions on patient tissue. Cryoablation systems have been used to reduce, or even eliminate, undesired electrical activity between adjacent cardiac tissues of the heart (arrhythmias). Radio frequency ablation systems ("RF ablation systems") use microwave energy to form heat-induced lesions on patient tissue and can also be used to treat some of the same conditions as cryoablation systems, including arrhythmias.

One common type of arrhythmia, atrial fibrillation, is a result of abnormal electrical signals interfering with the normal electrical signal propagation along the tissues of the heart. Atrial fibrillation often originates near the ostia of the pulmonary veins. Mapping catheters can be used to locate the abnormal electrical signals and medical ablation systems ("ablation systems") can be used to form lesions on patient tissue through which the abnormal electrical signals are propagated (e.g., tissue along the inner walls of the ostia (where the pulmonary veins open into the left atrium of the heart), or in proximity to the ostia). The cold-induced (or heat-induced) lesions can effectively block the initiation or propagation of the abnormal electrical signals, thereby preventing the abnormal electrical signals from interfering with the normal electrical signal propagation along the tissues of the heart.

BRIEF SUMMARY

In one embodiment, a mapping catheter includes an elongated body configured and arranged for insertion into patient vasculature. A distal end of the elongated body includes a distal portion that includes a plurality of electrodes, a proximal portion disposed proximal to the distal portion, and a reduced-dimension portion disposed between the proximal portion and the distal portion. The reduced-dimension portion has a cross-sectional dimension that is less than corresponding cross-sectional dimensions of both a proximally-positioned adjacent section of the distal portion and a distally-positioned adjacent section of the proximal portion. The distal end is formed, at least in part, from a memory shape material that bends into a preformed shape upon release from a confined space. The preformed shape includes a first loop formed, at least in part, by the distal portion. The first loop is transverse to a longitudinal axis of the proximal portion. The reduced-dimension portion is configured and arranged to bend such that the reduced-dimension section advances distally through the first loop when the first loop is held in a fixed position and a force is applied along the longitudinal axis of the proximal portion in a distal direction.

In another embodiment, an ablation system includes an ablation catheter, a guide tube, an expansion element, a mapping catheter, and a control module. The ablation catheter has a distal portion, a proximal portion, and a longitudinal length. The ablation catheter is configured and arranged for insertion into patient vasculature. The ablation catheter includes a body and defines at least one coolant outtake region extending along at least a portion of the ablation catheter. The guide tube is at least partially disposed in the ablation catheter. The expansion element is coupled to the distal portion of the body of the ablation catheter and is configured and arranged for ablating patient tissue. The mapping catheter includes an elongated body that is insertable into the guide tube. The elongated body includes a distal end that is extendable from a distal end of the guide tube. The distal end of the elongated body includes a distal portion that includes a plurality of electrodes, a proximal portion disposed proximal to the distal portion, and a reduced-dimension portion disposed between the proximal portion and the distal portion. The reduced-dimension portion has a cross-sectional dimension that is less than corresponding cross-sectional dimensions of both a proximally-positioned adjacent section of the distal portion and a distally-positioned adjacent section of the proximal portion. The distal end is formed, at least in part, from a memory shape material that bends into a preformed shape upon release from a confined space. The preformed shape includes a first loop formed, at least in part, by the distal portion. The first loop is transverse to a longitudinal axis of the proximal portion. The reduced-dimension portion is configured and arranged to bend such that the reduced-dimension section advances distally through the first loop when the first loop is held in a fixed position and a force is applied along the longitudinal axis of the proximal portion in a distal direction. The control module is coupled to the ablation catheter and the mapping catheter and is configured and arranged for controlling the mapping of electrical activity of the mapping catheter and the ablation of patient tissue by ablation catheter.

In yet another embodiment, a method of mapping a pulmonary vein includes guiding a mapping catheter in proximity to an ostium of a pulmonary vein. The mapping catheter includes an elongated body with a distal end formed, at least in part, from a memory shape material that bends into a preformed shape upon release from a confined space. The distal end of the elongated body includes a distal portion that includes a plurality of electrodes, a proximal portion disposed proximal to the distal portion, and a reduced-dimension portion disposed between the proximal portion and the distal portion. The reduced-dimension portion has a cross-sectional dimension that is less than corresponding cross-sectional dimensions of both a proximally-positioned adjacent section of the distal portion and a distally-positioned adjacent section of the proximal portion. The preformed shape includes a first loop formed, at least in part, by the distal portion. The first loop is transverse to a longitudinal axis of the proximal portion. The mapping catheter is inserted into the pulmonary vein such that the first loop abuts inner walls of the pulmonary vein. A force is provided distally along the axis of the proximal portion sufficient to cause the reduced-dimension portion to preferentially bend such that the reduced-dimension portion advances distally through the first loop. Electrical activity is mapped within walls of the pulmonary vein using a plurality of mapping electrodes disposed along the first loop.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4C is a schematic transverse cross-sectional view of multiple embodiments of some exemplary transverse profiles of the mapping catheters of FIGS. 4A and 4B, according to the invention;

FIG. 4D is a schematic transverse cross-sectional view of multiple embodiments of some exemplary transverse profiles of reduced-dimension portions of the mapping catheters of FIGS. 4A and 4B, according to the invention;

FIG. 4E is a schematic perspective view of one embodiment of the reduced-dimension portion of FIGS. 4A and 4B disposed between the distally-adjacent section and the proximally-adjacent section of FIGS. 4A and 4B, according to the invention;

FIG. 4F is a schematic perspective view of another embodiment of the reduced-dimension portion of FIGS. 4A and 4B disposed between the distally-adjacent section and the proximally-adjacent section of FIGS. 4A and 4B, according to the invention;

FIG. 4G is a schematic perspective view of yet another embodiment of the reduced-dimension portion of FIGS. 4A and 4B disposed between the distally-adjacent section and the proximally-adjacent section of FIGS. 4A and 4B, according to the invention;

DETAILED DESCRIPTION

The present invention is directed to the area of medical ablation systems and methods of making and using the medical ablation systems. The present invention is also directed to medical ablation systems having mapping catheters configured and arranged for facilitating the anchoring ability of the mapping catheters to patient tissue, as well as systems and methods for making and using the medical ablation systems and mapping catheters.

Mapping catheters include, but are not limited to, an elongated body and a plurality of electrodes disposed at the distal end of the body. The mapping catheters are configured and arranged for use with a medical ablation system during an ablation procedure. Examples of mapping catheters for use with medical ablation systems are found in, for example, U.S. Patent Applications Nos. 2008/0249518; and 2002/0177765, both of which are incorporated by reference.

Mapping catheters are typically used with medical ablation systems to map electrical activity along patient tissue. Mapping electrical activity can be useful for locating aberrant electrical activity, for example, in cardiac tissue. The mapping of the electrical activity can be performed prior to, during, or after an ablation procedure with an ablation system (e.g., a cryoablation system, an RF ablation system, or the like). Mapping catheters are described herein for use with cryoablation systems. It will be understood, however, that the mapping catheters may be used with other types of ablation systems as well including, for example, RF ablation systems. It will also be understood that mapping catheters may also be used with other types of medical therapeutic devices including, for example, electrical stimulation systems.

A cryoablation system can include an ablation catheter configured and arranged for transporting coolant to and from a target location within a patient, an expansion element disposed at a distal portion of the ablation catheter for ablating contacted patient tissue, a coolant source coupled to the ablation catheter for supplying the coolant, and a control module for controlling or monitoring one or more of the operations of the system (e.g., controlling coolant flow, monitoring ablation catheter pressure or temperature, or the like). The expansion element can be positioned at a target location in patient vasculature (e.g., the left atrium of the heart) and the coolant can be input to the ablation catheter and directed to the expansion element. When the coolant contacts the expansion element, the coolant absorbs heat and expands, thereby causing the expansion element to expand and reduce in temperature to a level low enough to ablate patient tissue upon contact. The coolant flows out of the expansion element and back to a proximal end of the ablation catheter. As the coolant flows out of the expansion element, the expansion element deflates and the ablation catheter may be removed from the patient vasculature.

Figure 1:
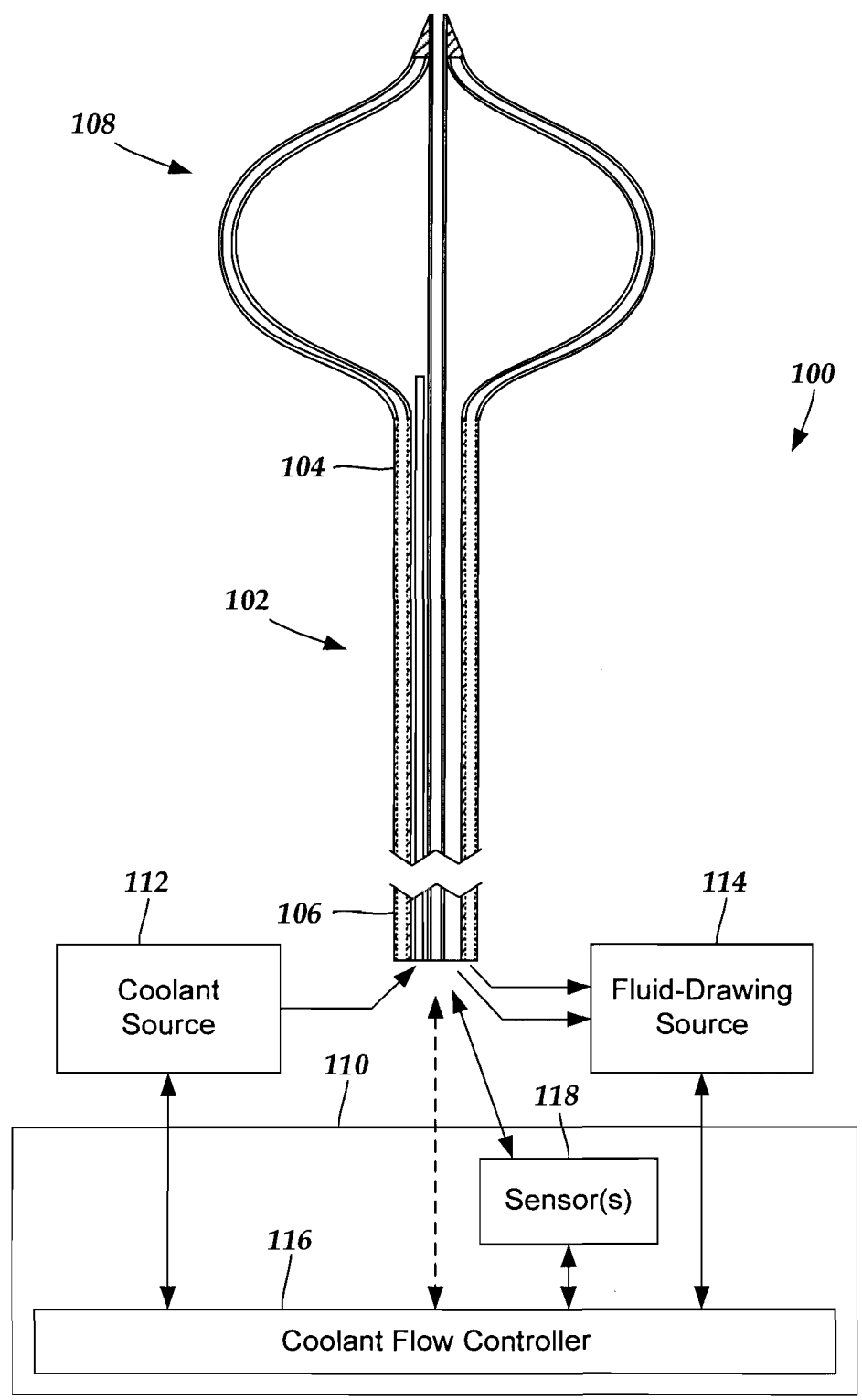
FIG. 1 is a schematic partial cross-sectional and partial block diagram view of one embodiment of a cryoablation system, according to the invention.

FIG. 1 illustrates schematically one embodiment of a cryoablation system 100. The cryoablation system 100 includes an ablation catheter 102 with a distal portion 104 and a proximal portion 106. An expansion element 108 is coupled to the distal portion 104 of the ablation catheter 102. A control module 110, a coolant source 112, and a fluid-drawing source 114 (e.g., a vacuum source, a pump, or the like) are each coupled to the proximal portion 106 of the ablation catheter 102. The control module 110 includes a coolant flow controller 116 to control the flow of coolant within the ablation catheter 102 to and from the expansion element 108. In at least some embodiments, the control module 104 also includes one or more sensors 118 for monitoring one or more conditions (e.g., pressure, temperature, or the like) within the ablation catheter 102.

In at least some embodiments, the coolant source 112 includes a coolant under pressure. A variety of different coolants may be used to provide a low enough temperature to ablate tissue upon contact. In preferred embodiments, the coolant is a low freezing point liquid with a low vaporization temperature which may be input to the ablation catheter 102 as a liquid that is sprayed into the expansion element 108, where the liquid coolant absorbs heat and is vaporized or atomized. Examples of suitable liquids include, but are not limited to, a liquefied gas (e.g., nitrogen, nitrous oxide, carbon dioxide, or the like), one or more chlorofluorocarbons, one or more hydrochlorofluorocarbons, ethanol mixtures, saline solutions, or the like. It will be understood that a combination of one or more coolants may be used in the cryoablation system 100.

Figure 2A:
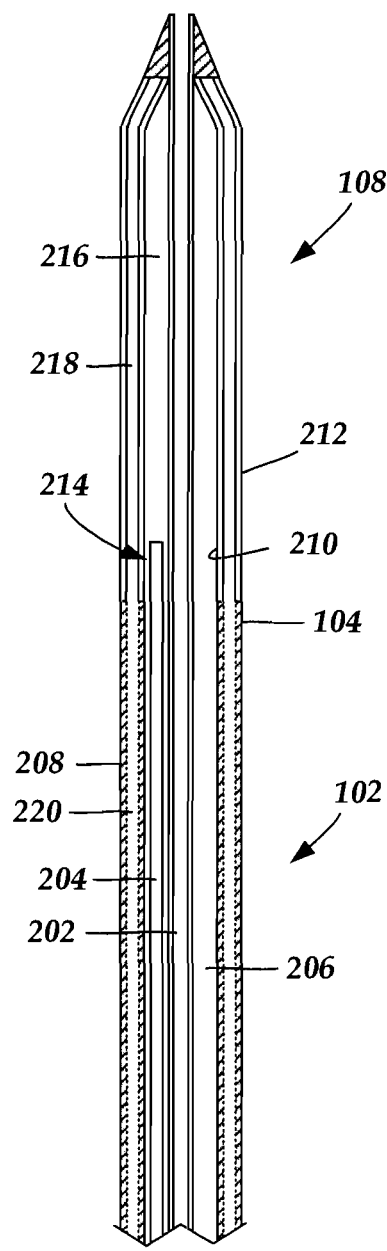
FIG. 2A is a schematic longitudinal cross-sectional view of one embodiment of an expansion element coupled to a distal portion of an ablation catheter of the cryoablation system of FIG. 1, the expansion element in a deflated configuration, according to the invention.

During a typical cryoablation procedure, the distal portion 104 of the ablation catheter 102 is inserted into patient vasculature for delivery of the expansion element 108 to one or more ablation sites. FIG. 2A is a schematic longitudinal cross-sectional view of one embodiment of the distal portion 104 of the ablation catheter 102 and the expansion element 108. In FIG. 2A, the expansion element 210 is shown in a deflated configuration. A guide tube 202, a coolant transfer lumen 204, and at least one coolant outtake region 206 are each disposed in a flexible body 208 of the ablation catheter 102.

In some embodiments, the expansion element 108 includes a single layer. In other embodiments, the expansion element 108 includes multiple layers. For example, in at least some embodiments, the expansion element 108 includes an inner layer 210 and an outer layer 212 disposed over the inner layer 210. FIGS. 1-3, 5, and 6 show the expansion element 108 having two layers. It will be understood that the expansion element 108 may, instead, only have a single layer, or may have more than two layers.

The expansion element 108 may be formed from any elastic or semi-elastic material, such as one or more thermoplastics (e.g., polyether block amide, or the like), or other plastics (e.g., nylon, urethane, or the like) that maintain elasticity over a wide range of temperatures, particularly at the temperature of the expanded coolant. In at least some embodiments, the expansion element 108 is semi-elastic, wherein the size of the expansion element 108 does not change in response to incremental changes in pressure that are below 5 psi (about $34.5 \times 10^3$ Pa).

The guide tube 202 may be formed from any flexible material (e.g., a thermoplastic, or the like) that maintains elasticity over a wide range of temperatures, particularly at the temperature of the expanded coolant. In at least some embodiments, the guide tube 202 is configured and arranged to receive a mapping catheter (see e.g., 302 in FIG. 3). In at least some embodiments, the guide tube 202 defines a lumen through which the mapping catheter 302 can be extended. In at least some embodiments, the mapping catheter 302 is extendable from a distal end of the guide tube 202, as discussed in more detail below, with respect to FIG. 3.

The guide tube 202 is optionally configured and arranged to receive a stiffening member (e.g., a stylet, or the like) to facilitate guiding of the ablation catheter 102 to a target location within patient vasculature by providing additional rigidity to the ablation catheter 102. In at least some embodiments, the guide tube 202 defines a lumen through which the stiffening member can be extended. In at least some embodiments, the guide tube extends along a longitudinal length of the ablation catheter 102 from the proximal portion (106 in FIG. 1) of the ablation catheter 102 to a position that is beyond the distal portion 104 of the ablation catheter 102.

The coolant transfer tube 204 extends along the longitudinal length of the ablation catheter 102 from the proximal portion (106 in FIG. 1) of the ablation catheter 102. The coolant transfer tube 204 defines a lumen. A proximal end of the lumen is coupled to the coolant source (112 in FIG. 1). The coolant transfer tube 204 includes a distal end 214 that opens into the expansion element 108.

The coolant outtake region 206 is configured and arranged to accommodate coolant exiting the expansion element 108. The coolant outtake region 206 extends along the longitudinal length of the ablation catheter 102 from the proximal portion (106 in FIG. 1) of the ablation catheter 102 to the expansion element 108. In some embodiments, the coolant outtake region 206 includes one or more tubes that define one or more lumens. In other embodiments, the coolant outtake region 206 includes one or more open regions within the body 208 of the ablation catheter 102 and exterior to the guide tube 202 and the coolant transfer tube 204.

In at least some embodiments, a proximal end of the expansion element 108 couples to the distal portion 104 of the ablation catheter 104. In at least some embodiments, the distal end of the expansion element 108 is coupled to the guide tube 202. In at least some embodiments, the expansion element 108 defines an inner expansion-element space 216 within the inner layer 210. In at least some embodiments, the inner expansion-element space 216 is in fluid communication with the distal end of the coolant transfer tube 204. In at least some embodiments, the inner expansion-element space 216 is in fluid communication with the at least one coolant outtake region 206. In at least some embodiments, the distal end 214 of the coolant transfer tube 204 extends beyond the distal portion of the ablation catheter 102 and into the inner expansion-element space 216. In at least some embodiments, the inner expansion-element space 216 is in fluid communication with the fluid-drawing source (114 in FIG. 1) via a proximal end of the coolant outtake region 206.

In at least some embodiments, a vacuum is maintained in a space between the inner layer 210 and the outer layer 212 (i.e., in an intra expansion-element space 218) of the expansion element 108. In at least some embodiments, the intra expansion-element space 218 is also in fluid communication with the fluid-drawing source 114 via a fluid pathway 220. In FIG. 2A, the fluid pathway 220 is shown as a space within the body 208 of the ablation catheter 102. In at least some embodiments, the fluid pathway 220 extends beyond the ablation catheter 102 (see e.g., FIGS. 4A-4B). In at least some embodiments, the fluid pathway 220 extends into a handle (see e.g., 402 in FIGS. 4A-4B) configured and arranged to couple to the proximal end 106 of the ablation catheter 102. In at least some embodiments, the fluid pathway 220 extends to the fluid-drawing source (114 in FIG. 1). In at least some embodiments, the fluid pathway 220 is in fluid communication with the coolant outtake region 206. In at least some embodiments, the fluid pathway 220 is in fluid communication with ambient air external to the ablation catheter 102. In at least some embodiments, the fluid pathway 220 is in fluid communication with ambient air external to a patient when the distal end 104 of the ablation catheter 102 is inserted into the patient. In at least some embodiments, the fluid pathway 220 is in fluid communication with ambient air external to the cryoablation system 100.

The distal end 214 of the coolant transfer tube 204 is configured and arranged to output coolant from the coolant transfer tube 204 to the inner expansion-element space 216. In at least some embodiments, the distal end 214 of the coolant transfer tube 204 is open. In at least some embodiments, the distal end 214 of the coolant transfer tube 204 defines one or more spray apertures. In at least some embodiments, the coolant is output as a sprayed liquid that vaporizes or atomizes as the liquid is output from the distal end 214 of the coolant transfer tube 204. In at least some embodiments, when the coolant enters the inner expansion-element space 216, the expansion element 108 absorbs heat and expands, thereby reducing the temperature of the expansion element 108 to a temperature sufficiently low enough to ablate patient tissue upon contact.

The reduction in temperature of the expansion element 108 may be due to one or more of the Joule-Thompson effect or the latent heat of vaporization. The Joule-Thompson effect describes the cooling effect that comes about when a compressed non-ideal gas expands into a region of low pressure (e.g., within the expansion element 108). The latent heat of vaporization describes heat being released as a result of the phase change from a liquid to a gas (e.g., the liquefied coolant vaporizing upon entering the expansion element 108).

Figure 2B:
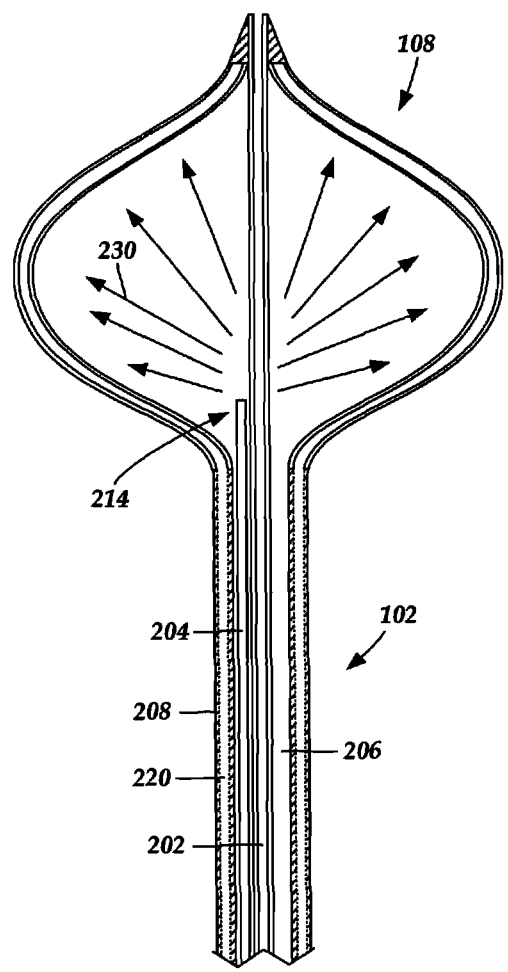
FIG. 2B is a schematic longitudinal cross-sectional view of one embodiment of an expansion element coupled to a distal portion of an ablation catheter of the cryoablation system of FIG. 1, the expansion element an inflated configuration, according to the invention.

FIG. 2B is a schematic longitudinal cross-sectional view of one embodiment of the expansion element 108 in an inflated configuration. Directional arrows, such as arrow 230, show the flow of coolant from the distal end 214 of the coolant transfer tube 204 to the inner expansion-element space 216. The expanded gas dissipates down the ablation catheter 102 along the coolant outtake region 206. In at least some embodiments, the fluid-drawing source (114 in FIG. 1) is used to draw the expanded, heated, and gaseous coolant along the coolant outtake region 206 from the expansion element 108 out the proximal end of the coolant outtake region 206. In at least some embodiments, the fluid-drawing source 114 is also used to maintain a vacuum in the intra expansion-element space 218. In at least some embodiments, the fluid-drawing source 114 maintains a vacuum in the intra expansion-element space 218 via the fluid pathway 220.

The ablation catheter 102 may be inserted in patient vasculature and guided to an ablation site, such as the ostia of one or more of the pulmonary veins in the left atrium of the heart of the patient. In at least some embodiments, the expansion element 108 is maintained in a vacuum during insertion. Sometime after the expansion element is in proximity to the ablation site, coolant from the coolant source (106 in FIG. 1) is released into the ablation catheter 102. In at least some embodiments, the coolant source 106 includes a pressurized container or pump. In at least some embodiments, the lower pressure in the expansion element 108 draws the coolant along the coolant transfer tube 104 and into the expansion element 108. In at least some embodiments, the fluid-drawing source (114 in FIG. 1) may be used to control the rate of flow of the coolant within the ablation catheter 102. The rate of flow of the coolant within the ablation catheter 102 may be adjusted to a rate appropriate to the specific type of operation.

Typically, electrical activity within patient tissue surrounding the ostium of the pulmonary vein being ablated is monitored and mapped prior to ablation. Potential foci for the arrhythmia are identified based on the electrical map. The foci may be ablated by forming a lesion (e.g., using the cryoablation system (or RF ablation system)) along the inner wall of the pulmonary vein, or along tissue of the left atrium in proximity to the ostia of the pulmonary vein, to isolate the heart from the aberrant electrical activity along the pulmonary vein. The efficacy of the electrical isolation may be checked by remapping the pulmonary vein during or after ablation. In at least some embodiments, the mapping catheter may be left in place during ablation in order to allow the pulmonary vein to be remapped at the same location of the ablation.

Figure 3:
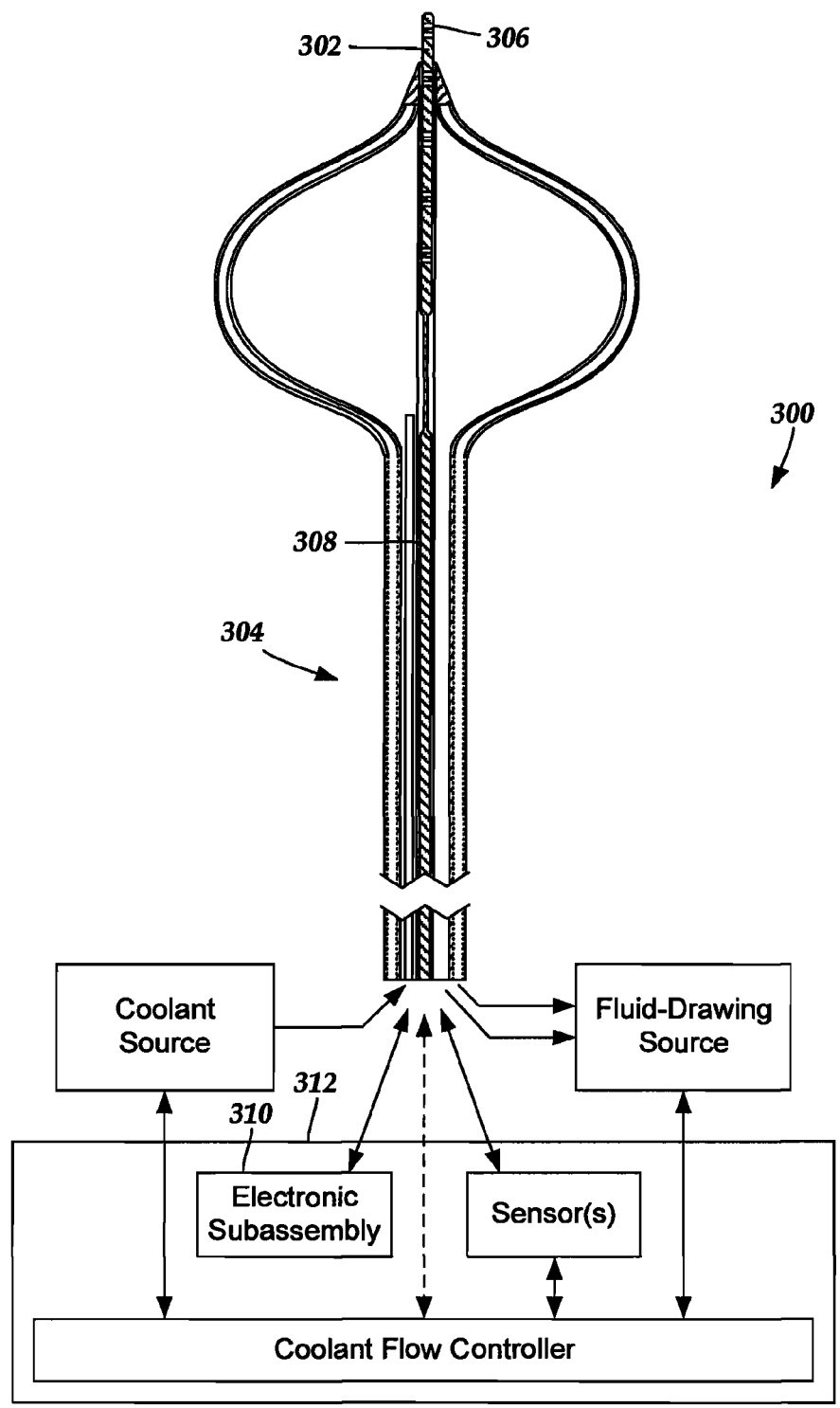
FIG. 3 is a schematic partial cross-sectional and partial block diagram view of another embodiment of a cryoablation system that includes a mapping catheter insertable into, and extendable from, a distal end of an ablation catheter, according to the invention.

Effective treatment of atrial fibrillation may depend on the ability of the ablation system to obtain a successful electrical map of the heart at the antrum or ostium of one or more of the pulmonary veins before and after an ablation procedure. In at least some embodiments, a mapping catheter is used to perform electrical mapping. FIG. 3 is a schematic partial cross-sectional and partial block diagram view of another embodiment of a cryoablation system 300 that includes a mapping catheter 302 insertable into, and extendable from, an ablation catheter 304. In at least some embodiments, one or more mapping electrodes 306 are disposed along a distal end of the mapping catheter 302. In at least some embodiments, the mapping catheter 302 extends through a lumen 308 defined along at least a portion of the ablation catheter 304.

In at least some embodiments, the electrodes 306 are electrically coupled to an electronic subassembly 310 disposed in a control module 312 and configured and arranged to control the operation of the electrodes 306. In at least some embodiments, the electrodes 306 are electrically coupled to the control module 312 via one or more conductors (not shown) extending along at least a portion of the mapping catheter 302.

In at least some embodiments, once the ablation catheter 304 is positioned in proximity to a potential ablation site, the distal end of the mapping catheter 302 is extended from the ablation catheter 304. In at least some embodiments, once the distal end of the mapping catheter 320 is extended from the ablation catheter 304, the distal end of the mapping catheter 302 bends into a preformed shape that includes a loop along an axis that is approximately transverse to the axis of the ablation catheter 304 (see e.g., FIG. 4B). Examples of mapping catheters and associated ablation catheters can be found in U.S. Patent Applications Nos. 2008/0249518; and 2002/0177765, both of which are incorporated by reference.

It is desirable for an ablation system to maintain a stable position and orientation during an ablation procedure to ensure accurate electrical mapping and accurate ablation. During at least a portion of the ablation procedure, the mapping catheter may be the only portion of an ablation system physically contacting the pulmonary vein. At least some conventional ablation systems are configured and arranged such that a transverse loop of the mapping catheter is the only portion of the ablation system anchoring the ablation system to the pulmonary vein. When a loop is the only portion of an ablation system anchoring the ablation system to a pulmonary vein, the ablation system may pivot, tilt, rock, or even shift position, thereby maintaining an unstable position or orientation with respect to the pulmonary vein.

In at least some embodiments, the mapping catheter 302 includes an elongated body having a proximal portion coupled to a loop formed by a distal portion of the elongated body that is transverse to an axis of the proximal portion. In at least some embodiments, once the loop is positioned against patient tissue, a reduced-dimension portion of the mapping catheter 302 can be bent such that the reduced-dimension portion can be advanced distally through the loop. In at least some embodiments, by advancing the reduced-dimension portion through the loop, the ablation system 300 may be more stably anchored to patient tissue during at least a portion of an ablation procedure.

Figure 4A:
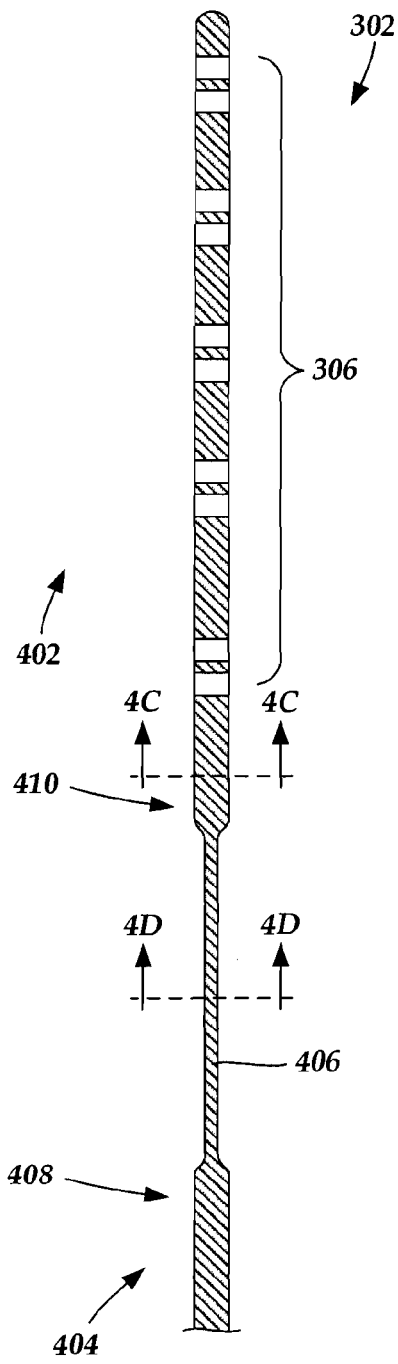
FIG. 4A is a schematic side view of one embodiment of a distal end of the mapping catheter of FIG. 3 in a substantially-straight configuration, the mapping catheter having an elongated body that includes a reduced-dimension portion proximal to a plurality of mapping, electrodes, according to the invention.

FIG. 4A is a schematic side view of one embodiment of a distal end of the mapping catheter 302 in a substantially-straight configuration. The mapping catheter 302 may be in a substantially-straight configuration when, for example, the mapping catheter 302 is disposed in a confined space (e.g., when the mapping catheter 302 is disposed in the lumen 308 of the ablation catheter 302). It will be understood that a "substantially-straight configuration" may be curved, particularly when the mapping catheter 302 is disposed in a confined space that is curved, such as a curved lumen.

Figure 4B:
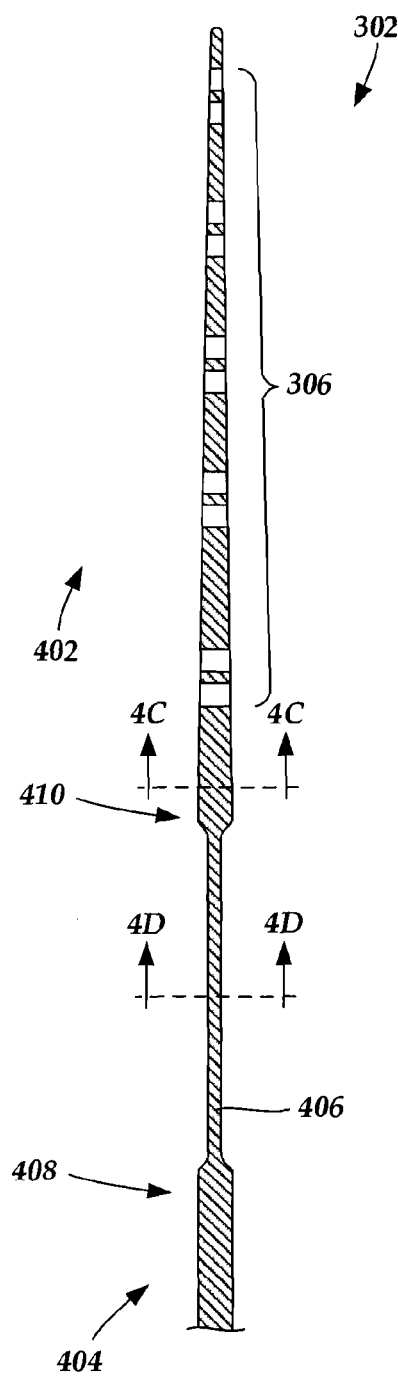
FIG. 4B is a schematic side view of another embodiment of a distal end of the mapping catheter of FIG. 3 in a substantially-straight configuration, the mapping catheter including a reduced-dimension portion and a distal portion that tapers in a distal direction, according to the invention.

The mapping catheter 302 includes a proximal portion 404 and a distal portion 402. At least some of the electrodes 306 are disposed on the distal portion 402 of the mapping catheter 302. In some embodiments, the distal portion 402 is isodiametric. In other embodiments, as shown in FIG. 4B, at least a part of the distal portion 402 tapers towards in a distal direction. The mapping catheter 302 also includes a reduced-dimension portion 406 positioned between the proximal portion 404 and the distal portion 402. In at least some embodiments, the reduced-dimension portion 406 tapers. In at least some embodiments, at least one of the electrodes 306 is disposed on the reduced-dimension portion 406. The proximal portion 404 includes a section 408 that is positioned proximally-adjacent to the reduced-dimension portion 406. The distal portion 402 includes a section 410 that is positioned distally-adjacent to the reduced-dimension portion 406.

In at least some embodiments, the distal end of the mapping catheter 302 is formed, at least in part, using a shape memory material (e.g., nitinol, or the like). For example, in at least some embodiments, the mapping catheter 302 has a nitinol core and a shell formed over the nitinol core that is formed from a non-conductive material (e.g., one or more polymers, or the like or combinations thereof). In at least some embodiments, the mapping catheter 302 may be preformed in a desired shape that may be reversibly straightened when the mapping catheter 302 is disposed in a confined space (e.g., the lumen 308 of the ablation catheter 302).

In at least some embodiments, at least a portion of the mapping catheter 302 has a transverse profile that is round. It will be understood that one or more portions of the mapping catheter 302 may have a transverse profile (see e.g., exemplary transverse profiles 410-417 of FIG. 4C) that is at least one other shape (either geometric or irregular) besides round. For example, at least one of the proximal portion 404 or the distal portion 402 of the mapping catheter 302 may have a transverse profile that is ovoid, triangular, rectangular, pentagonal, hexagonal, heptagonal, octagonal, nonagonal, decagonal, cross-shaped, star-shaped, or the like.

The electrodes 306 may be any suitable shape for contacting patient tissue when the mapping catheter 302 is configured into a preformed shape (e.g., when a distal end of the mapping catheter 302 is formed into a looped configuration, as shown in FIGS. 5A-5C and 8A-8C). For example, the electrodes 306 may be annular, C-shaped, geometrically shaped (e.g., ovoid, triangular, rectangular, pentagonal, hexagonal, heptagonal, octagonal, nonagonal, decagonal, or the like), irregularly shaped, or the like or combinations thereof.

Any number of electrodes 306 may be disposed on the mapping catheter 302 suitable for electrically mapping a region of patient tissue. For example, there may be one, two, three, four, five, six, seven, eight, nine, ten, eleven, twelve, sixteen, twenty, twenty-four, or more electrodes 306. It will be understood that there may be other numbers of electrodes 306 disposed on the mapping catheter 302.

The distal portion 402 of the mapping catheter 302 can be formed having any transverse diameter suitable for forming into one or more loops sized for removable placement around an inner perimeter of a blood vessel (e.g., an ostium of a pulmonary vein, or the like) for electrical mapping. The reduced-dimension portion 406 is a region that is more flexible than the remaining portions of the mapping catheter 302 that are extendable from the ablation catheter 102 along at least one dimension. In at least some embodiments, when a force is applied to the mapping catheter 302, the increased flexibility of the reduced-dimension portion 406 causes the reduced-dimension portion 406 to preferentially bend along the at least one dimension. In at least some embodiments, the reduced-dimension portion 406 is disposed proximal to the electrodes 306. In at least some embodiments, at least one electrode is disposed on the reduced-dimension portion 406. In at least some embodiments, at least one electrode is disposed proximal to the reduced-dimension portion 406.

As discussed above, in at least some embodiments the transverse profile of the distal portion 402 of the mapping catheter 302 is isodiametric. In at least some embodiments, the transverse profile of the proximal portion 404 of the mapping catheter 302 is isodiametric. In at least some embodiments, the transverse profile of the portions of the mapping catheter 302 that are extendable from the ablation catheter 102 are isodiametric except for the reduced-dimension portion 406.

In at least some embodiments, the reduced-dimension portion 406 is made more flexible than the remaining portions of the mapping catheter 302 that are extendable from the ablation catheter 102 by selecting at least one of the size or the shape of the transverse profile (e.g., the transverse cross-sectional shape) of the reduced-dimension portion 406 (see e.g., transverse profiles 420 and 421 of FIG. 4D) so that it differs from at least one of the size or the shape of the transverse profile of the remaining portions of the mapping catheter 302 that are extendable from the ablation catheter 102 (see e.g., exemplary transverse profiles 410-417 of FIG. 4C).

For example, in at least some embodiments, the transverse profile of the proximal portion 404 and the distal portion 402 of the distal end of the mapping catheter 302 are round, while the transverse profile of the reduced-dimension portion 406 is rectangular 421. Thus, in at least some embodiments, when the reduced-dimension portion 406 has a rectangular 421 transverse profile, the reduced-dimension portion 406 has two perpendicular dimensions that form a height 424 and a width 426, respectively. Thus, the transverse profile of the reduced-dimension portion 406 may have a variety of different aspect ratios (i.e., the ratio of the larger diameter (424 in FIG. 4C) to the smaller diameter (426 in FIG. 4C)).

In at least some embodiments, the transverse profile of the reduced-dimension portion 406 has an aspect ratio of no greater than approximately 1:1. In at least some embodiments, the transverse profile of the reduced-dimension portion 406 has an aspect ratio of no greater than approximately 2:1. In at least some embodiments, the transverse profile of the reduced-dimension portion 406 has an aspect ratio of no greater than approximately 3:1. In at least some embodiments, the transverse profile of the reduced-dimension portion 406 has an aspect ratio of no greater than approximately 4:1. In at least some embodiments, the transverse profile of the reduced-dimension portion 406 has an aspect ratio of no greater than approximately 5:1. In at least some embodiments, the transverse profile of the reduced-dimension portion 406 has an aspect ratio of no greater than approximately 6:1. In at least some embodiments, the transverse profile of the reduced-dimension portion 406 has an aspect ratio of no greater than approximately 7:1. In at least some embodiments, the transverse profile of the reduced-dimension portion 406 has an aspect ratio of no greater than approximately 8:1. In at least some embodiments, the transverse profile of the reduced-dimension portion 406 has an aspect ratio of no greater than approximately 9:1. In at least some embodiments, the transverse profile of the reduced-dimension portion 406 has an aspect ratio of no greater than approximately 10:1.

In at least some embodiments, the smallest transverse dimension of the reduced-dimension portion 406 is less than the largest transverse dimension of the proximally-adjacent section 408 and the largest transverse dimension 440 of the distally-adjacent section 410. FIG. 4E is a schematic perspective view of one embodiment of a reduced-dimension portion 406 disposed between the distally-adjacent section 410 and the proximally-adjacent section 408. In FIG. 4E, the smallest transverse dimension 426 of the reduced-dimension portion 406 is less than the largest transverse dimension 440 of the proximally-adjacent section 408. In FIG. 4E, the largest transverse dimension 424 of the reduced-dimension portion 406 is greater than the smallest transverse dimension 426, but is less than the largest transverse dimension 440 of the proximally-adjacent section 408. In at least some embodiments, the proximally-adjacent section 408 and the distally-adjacent section 410 are equal in diameter.

In at least some embodiments, the largest transverse dimension of the reduced-dimension portion 406 is equal to, or greater than, the largest transverse dimension of the proximally-adjacent section 408 and the largest transverse dimension 440 of the distally-adjacent section 410. FIG. 4F shows the largest transverse dimension 424 of the reduced-dimension portion 406 being greater than the smallest transverse dimension 426 and equal to the largest transverse dimension 440 of the proximally-adjacent section 408. FIG. 4G shows the largest transverse dimension 424 of the reduced-dimension portion 406 being greater than the smallest transverse dimension 426 and greater than the largest transverse dimension 440 of the proximally-adjacent section 408.

In at least some embodiments, the smallest transverse dimension 426 of the reduced-dimension portion 406 is no more than one quarter the length of at least one of the largest transverse dimension of the proximally-adjacent section 408 or the largest transverse dimension 440 of the distally-adjacent section 410. In at least some embodiments, the smallest transverse dimension 426 of the reduced-dimension portion 406 is no more than one third the length of at least one of the largest transverse dimension of the proximally-adjacent section 408 or the largest transverse dimension 440 of the distally-adjacent section 410. In at least some embodiments, the smallest transverse dimension 426 of the reduced-dimension portion 406 is no more than one half the length of at least one of the largest transverse dimension of the proximally-adjacent section 408 or the largest transverse dimension 440 of the distally-adjacent section 410. In at least some embodiments, the smallest transverse dimension 426 of the reduced-dimension portion 406 is no more than one two-thirds the length of at least one of the largest transverse dimension of the proximally-adjacent section 408 or the largest transverse dimension 440 of the distally-adjacent section 410. In at least some embodiments, the smallest transverse dimension 426 of the reduced-dimension portion 406 is no more than three-quarters the length of at least one of the largest transverse dimension of the largest transverse dimension of the proximally-adjacent section 408 or the largest transverse dimension 440 of the distally-adjacent section 410.

In at least some embodiments, when the distal end of the mapping catheter 302 is extended from the ablation catheter 102, the distal end of the mapping catheter 302 is configured and arranged to bend into a looped configuration. In at least some embodiments, the distal end of the mapping catheter 302 is formed from a shape memory material configured and arranged to bend into a preformed shape that includes at least one loop without external aid when the distal end of the mapping catheter 302 is extended from the ablation catheter 102. In at least some embodiments, the one or more loops extend approximately transverse to the axis of the proximal portion 404. In at least some embodiments, the one or more loops extend approximately transverse to the axis of the ablation catheter 102.

Figures 5A, 5B:
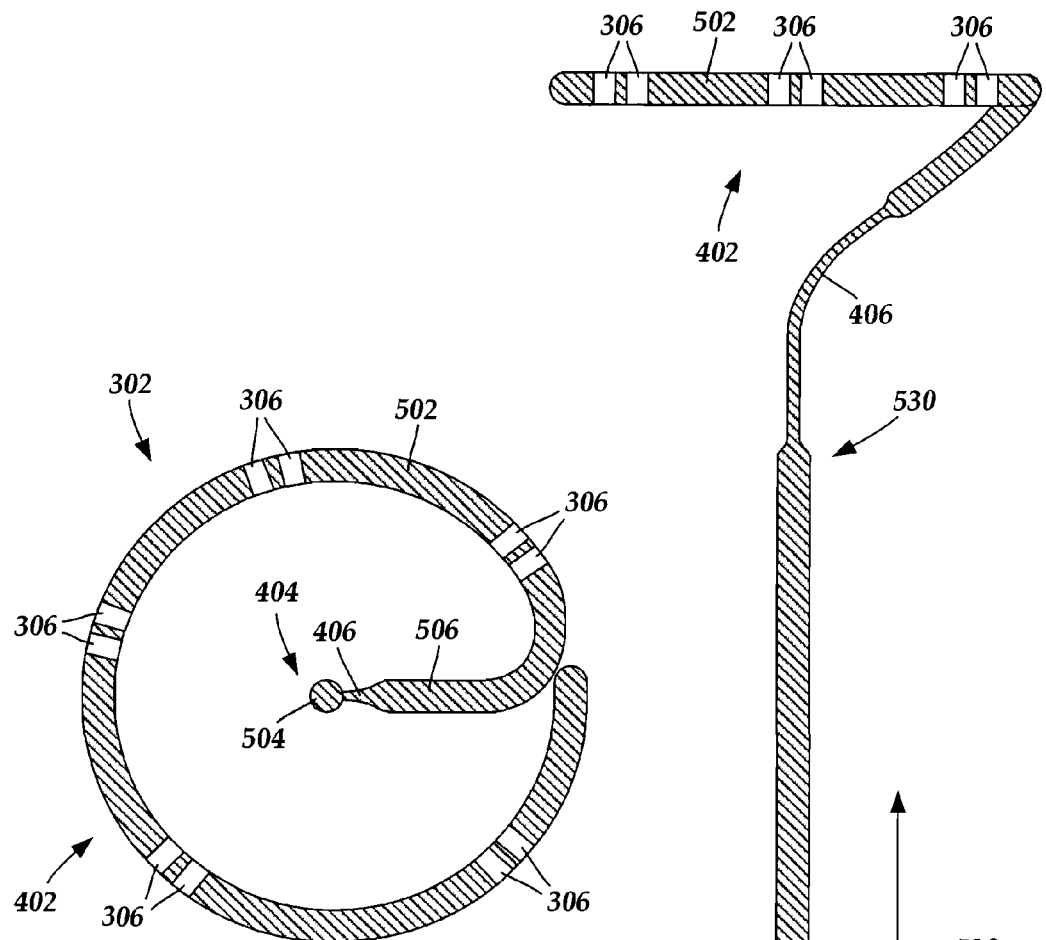
FIG. 5A is a schematic bottom view of one embodiment of the distal end of the mapping catheter of FIG. 4A disposed in a configuration having a substantially-straight proximal portion and a distal portion bent into a loop, the loop transverse to a longitudinal axis of the proximal portion, according to the invention.
FIG. 5B is a schematic side view of one embodiment of the distal end of the mapping catheter of FIG. 4A disposed in a configuration having a substantially-straight proximal portion and a distal portion bent into a loop, the loop transverse to a longitudinal axis of the proximal portion, according to the invention.

FIGS. 5A and 5B are a schematic side view and bottom view, respectively, of one embodiment of the distal end of the mapping catheter 302 having an elongated body 500 that includes the distal portion 402, the proximal portion 404, and the reduced-dimension portion 406. The distal portion 402 is configured into a shape that includes a loop 502. At least one of the electrodes 306 is disposed on the loop 502. In at least some embodiments, the loop 502 is formed by bending the distal portion 402 at least three-quarters of a full circle. In at least some embodiments, the loop 502 is formed by bending the distal portion 402 at least one full circle. In at least some embodiments, the loop 502 is formed by bending the distal portion 402 at least one-and-a-quarter full circles. In at least some embodiments, the loop 502 tapers in a distal direction (see e.g., the distal portion 402 of FIG. 4B). In at least some embodiments, the smallest transverse dimension 426 of the reduced-dimension portion 406 is greater than a smallest transverse dimension of the tapered loop 502.

The loop 502 can be formed to any suitable diameter for mapping electrical activity of a region of patient tissue. In at least some embodiments, the reduced-dimension portion 406 extends at least 1 cm along the body 500 of the mapping catheter 302. In at least some embodiments, the reduced-dimension portion 406 extends at least 2 cm along the body 500 of the mapping catheter 302. In at least some embodiments, the reduced-dimension portion 406 extends at least 3 cm along the body 500 of the mapping catheter 302. In at least some embodiments, the reduced-dimension portion 406 extends at least 4 cm along the body 500 of the mapping catheter 302. In at least some embodiments, the reduced-dimension portion 406 extends at least 5 cm along the body 500 of the mapping catheter 302. In at least some embodiments, the reduced-dimension portion 406 extends at least 6 cm along the body 500 of the mapping catheter 302. In at least some embodiments, the reduced-dimension portion 406 extends at least 7 cm along the body 500 of the mapping catheter 302.

In at least some embodiments, the reduced-dimension portion 406 is configured and arranged to bend when the loop 502 is held in a fixed position (such as being extended around inner walls of a patient blood vessel) and a force is applied distally approximately along a longitudinal axis of the proximal portion 404 of the mapping catheter 302, as shown by directional arrow 520. In at least some embodiments, when such a force is applied, the reduced-dimension portion 406 is configured and arranged to preferentially bend to advance the proximal portion 404 distally. In at least some embodiments, when such a force is applied, the reduced-dimension portion 406 is configured and arranged to preferentially bend such that the reduced-dimension portion 406 advances distally through the loop 502. In at least some embodiments, when such a force is applied, the reduced-dimension portion 406 is configured and arranged to preferentially bend such that a section 530 of the mapping catheter 302 proximally adjacent to the reduced-dimension portion 406 advances distally through the loop 502. In at least some embodiments, the amount of force applied to bend the reduced-dimension portion 406 can be less than the amount of force to bend the remaining portions of the mapping catheter 302.

Figure 5C:
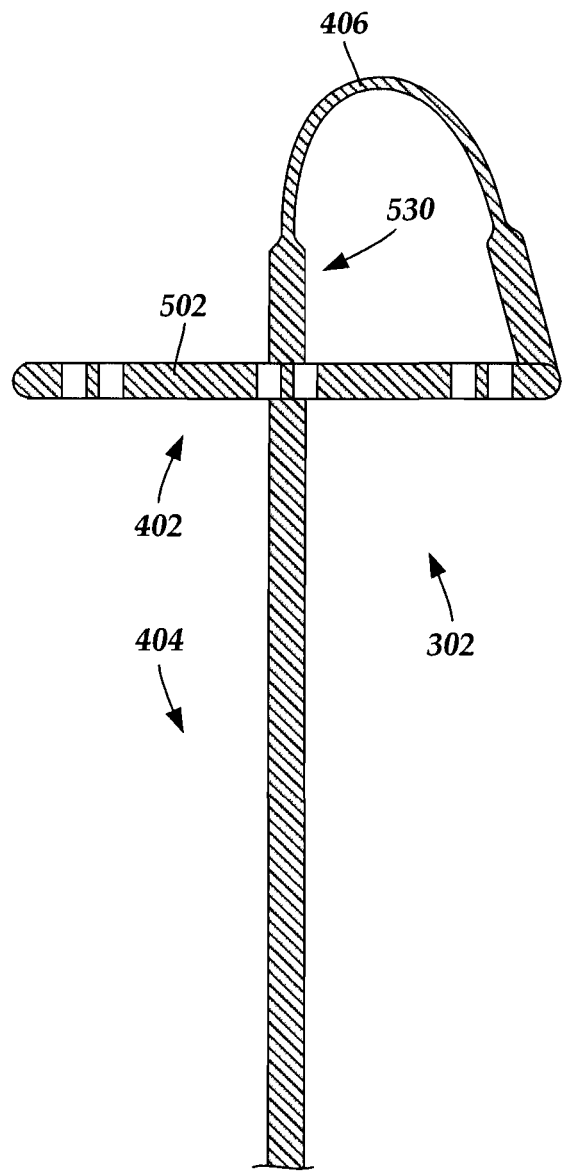
FIG. 5C is a schematic side view of one embodiment of the distal end of the mapping catheter of FIG. 4A disposed in the looped configuration of FIG. 5A and bent along a reduced-dimension portion of the mapping catheter such that the reduced-dimension portion is advanced distally through a loop formed by a distal portion of the mapping catheter, according to the invention.

FIG. 5C is a schematic side view of one embodiment of the distal end of the mapping catheter 302. The reduced-dimension portion 406 is bent such that the reduced-dimension portion 406 and the section 530 of the mapping catheter 302 proximally adjacent to the reduced-dimension portion 406 is extended through the loop 502.

Figure 6A:
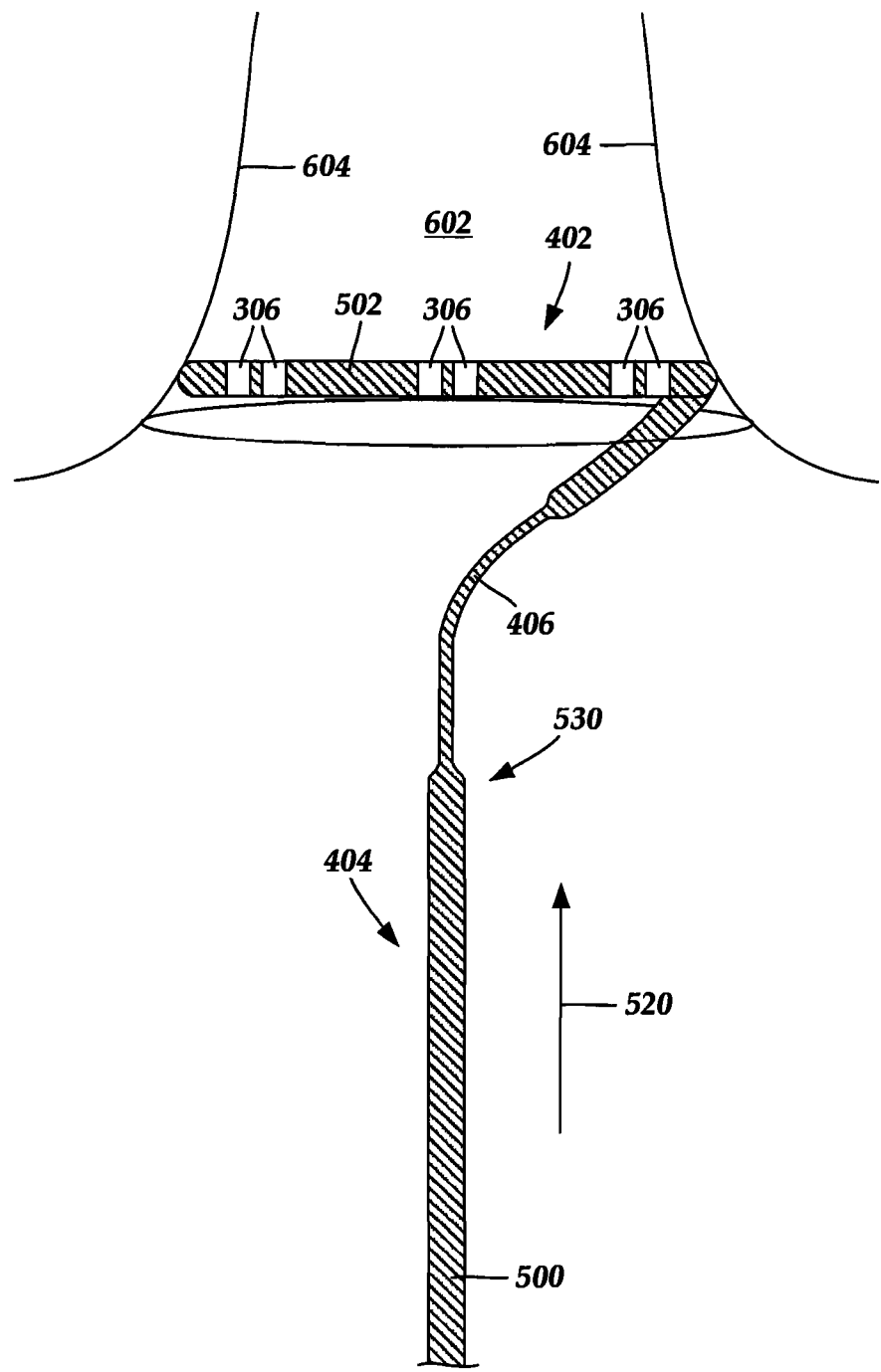
FIG. 6A is a schematic side view of one embodiment of the mapping catheter of FIG. 4A disposed in the looped configuration of FIG. 5B and disposed in an ostium of a pulmonary vein such that a loop formed by the distal portion of the mapping catheter abuts patient tissue in proximity to the ostium, according to the invention.
Figure 6B:
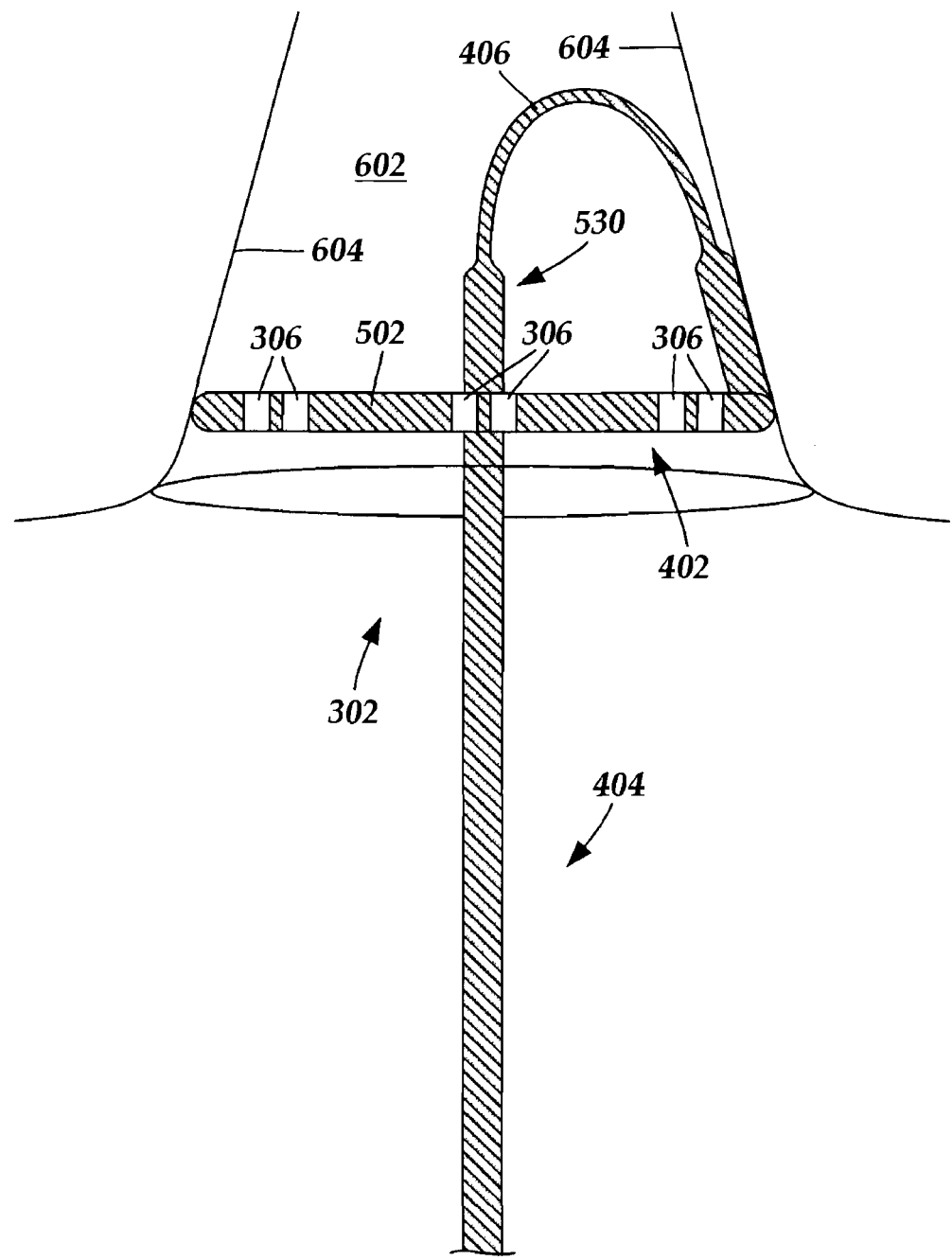
FIG. 6B is a schematic side view of one embodiment of the mapping catheter of FIG. 6A disposed in an ostium of a pulmonary vein, the mapping catheter bent along a reduced-dimension portion of the mapping catheter such that the reduced-dimension is advanced distally through a loop formed by a distal portion of the mapping catheter, according to the invention.

The mapping catheter 302 can be positioned to abut patient tissue to be electrically mapped. The distal portion 402 of the mapping catheter 302 can be extended from the ablation catheter 102 and bent to form the loop 502. The mapping catheter 302 can be positioned against patient tissue such that the electrodes 306 contact patient tissue at the site to be mapped. FIG. 6A is a schematic side view of one embodiment of the distal end of the mapping catheter 302 formed into a looped configuration and disposed in an ostium 602 of a pulmonary vein such that the loop 502 of the mapping catheter 302 abuts patient tissue along inner walls 604 of the ostium 602. In FIGS. 6A-6B the walls 604 are shown as being transparent for clarity of illustration.

A force may be applied to the mapping catheter 302 in the direction indicated by directional arrow 520. The force causes the reduced-dimension portion 406 of the mapping catheter 302 to preferentially bend such that the reduced-dimension portion 406 of the mapping catheter 302 advances distally through the loop 502. In at least some embodiments, the force causes the reduced-dimension portion 406 of the mapping catheter 302 to preferentially bend such that the section 530 of the mapping catheter 302 proximally adjacent to the reduced-dimension portion 406 advances distally through the loop 502.

FIG. 6B is a schematic side view of one embodiment of the distal end of the mapping catheter 302 disposed in the ostium 602 of a pulmonary vein such that the loop 502 of the mapping catheter 302 abuts patient tissue 604 in proximity to the ostium 602. The reduced-dimension portion 406 of the mapping catheter 302 is bent such that the reduced-dimension portion 406 of the mapping catheter 302 extends through the loop 502. In at least some embodiments, the reduced-dimension portion 406 is bent such that the section 530 of the mapping catheter 302 proximally adjacent to the reduced-dimension portion 406 extends through the loop 502.

In at least some embodiments, when the reduced-dimension portion 406 extends through the loop 502, the mapping catheter 302 anchors more stably to the inner walls 604 of the ostium 602. In at least some embodiments, when the reduced-dimension portion 406 extends distally through the loop 502, the ability of the mapping catheter 302 to tilt, pivot, rock, or shift position within the ostium 602 is reduced from when the reduced-dimension portion 406 is positioned proximal to the loop 502. In at least some embodiments, the reduced-dimension portion 406 is extended distally through the loop 502 such that the reduced-dimension portion 406 abuts patient tissue 604.

Figures 7A, 7B:
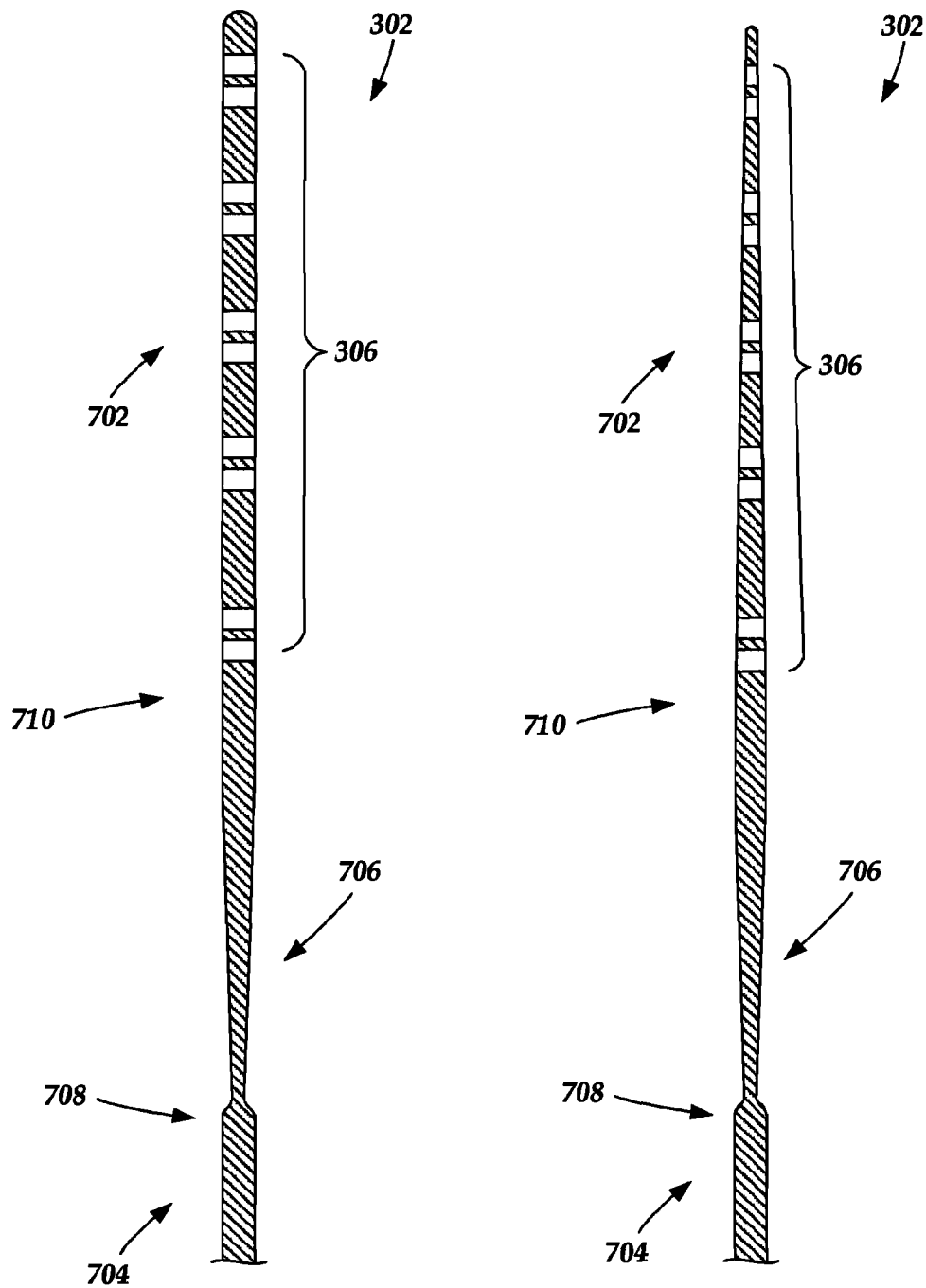
FIG. 7A is a schematic side view of yet another embodiment of a distal end of the mapping catheter of FIG. 3 in a substantially-straight configuration, the mapping catheter having an elongated body that includes a reduced-dimension portion proximal to a plurality of mapping electrodes, according to the invention.
FIG. 7B is a schematic side view of another embodiment of a distal end of the mapping catheter of FIG. 3 in a substantially-straight configuration, the mapping catheter including a reduced-dimension portion and a distal portion that tapers in a distal direction, according to the invention.

FIG. 7A is a schematic side view of another embodiment of the distal end of the mapping catheter 302 disposed in a substantially-straight configuration. The mapping catheter 302 includes a distal portion 702 and a proximal portion 704. The electrodes 306 are disposed on the distal portion 702 of the mapping catheter 302. In some embodiments, the distal portion 702 is isodiametric. In other embodiments, as shown in FIG. 7B, the distal portion 702 tapers in a distal direction. The mapping catheter 302 also includes a reduced-dimension portion 706 positioned between the distal portion 702 and the proximal portion 704. In at least some embodiments, the reduced-dimension portion 706 tapers in a proximal direction. In at least some embodiments, at least one of the electrodes 306 is disposed on the reduced-dimension portion 706. The proximal portion 704 includes a section 708 that is positioned proximally-adjacent to the reduced-dimension portion 706. The distal portion 702 includes a section 710 that is positioned distally-adjacent to the reduced-dimension portion 706.

In at least some embodiments, when the distal end of the mapping catheter 302 is extended from the ablation catheter 102, the mapping catheter 302 bends into a looped configuration that includes two loops. In at least some embodiments, the distal portion 702 bends to form a first loop. In at least some embodiments, the reduced-dimension 706 bends to form a second loop. In at least some embodiments, both loops are parallel to one another. In at least some embodiments, at least one of the loops is transverse to a longitudinal axis of the proximal portion 704. In at least some embodiments, both loops are transverse to a longitudinal axis of the proximal portion 704.

Figures 8A, 8B:
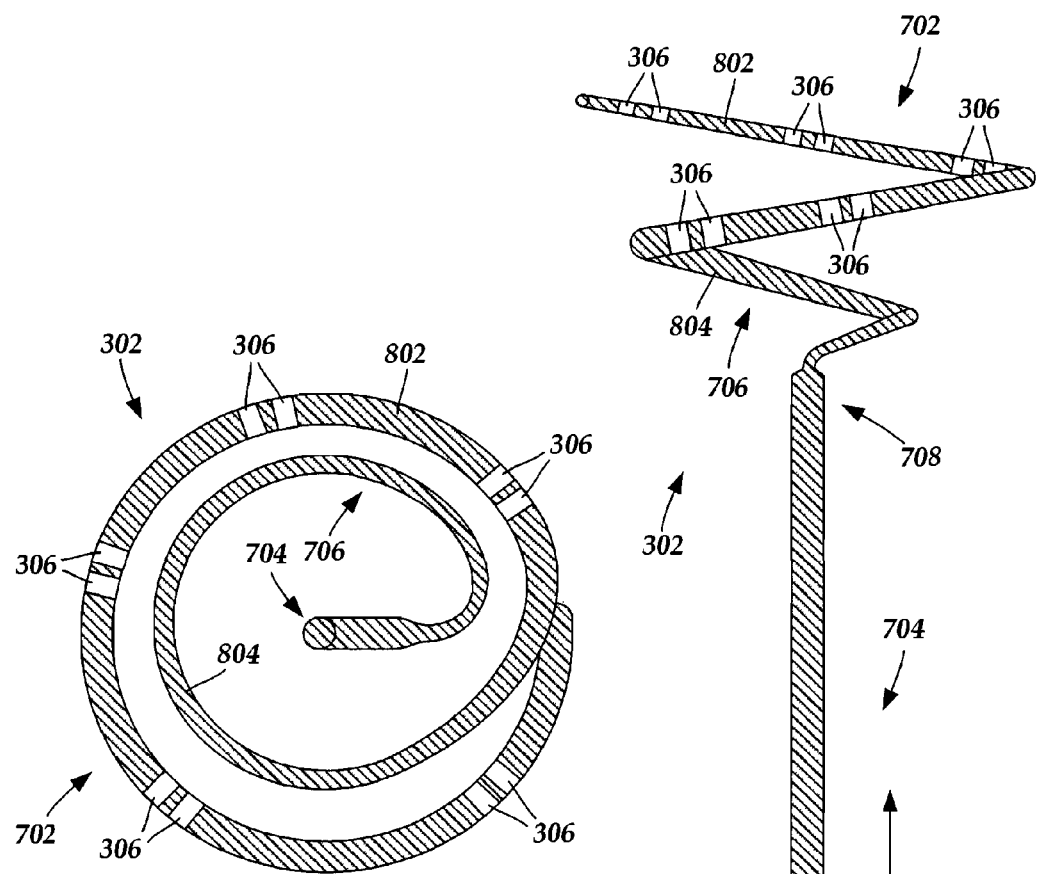
FIG. 8A is a schematic bottom view of one embodiment of the distal end of the mapping catheter of FIG. 7A disposed in a configuration having a substantially-straight proximal portion, a first loop formed by a distal portion, and a second loop formed by a tapering reduced-dimension portion proximal to the first loop, the loops both transverse to a longitudinal axis of the proximal portion, according to the invention.
FIG. 8B is a schematic side view of one embodiment of the distal end of the mapping catheter of FIG. 7B disposed in a looped configuration having a substantially-straight proximal portion, a first loop formed by a tapered distal portion, and a second loop formed by a tapering reduced-dimension portion proximal to the first loop, the loops both transverse to a longitudinal axis of the proximal portion, according to the invention.

FIGS. 8A and 8B are a schematic side view and bottom view, respectively, of alternate embodiments of a distal end of the mapping catheter 302 having an elongated body 800 that includes the distal portion 702, the proximal portion 704, and the reduced-dimension portion 706 disposed between the distal portion 702 and the proximal portion 704. In FIG. 8A, the distal portion 702 is shown as being isodiametric, as shown in FIG. 7A. In FIG. 8B, the distal portion 702 is shown tapering in a distal direction, as shown in FIG. 7B. The distal portion 702 (as shown in both FIGS. 8A and 8B) is configured into a shape that includes a first loop 802. At least one of the electrodes 306 is disposed on the first loop 802. In at least some embodiments, at least one electrode is disposed proximal to the first loop 802. In at least some embodiments, at least one electrode is disposed on the reduced-dimension portion 706. In at least some embodiments, at least one electrode is disposed proximal to the reduced-dimension portion 706.

In at least some embodiments, the reduced-dimension portion 706 bends to form a second loop 804. In at least some embodiments, the second loop 804 is formed by bending the reduced-dimension portion 706 at least three-quarters of a full circle. In at least some embodiments, the second loop 804 is formed by bending the reduced-dimension portion 706 at least one full circle. In at least some embodiments, the second loop 804 is formed by bending the reduced-dimension portion 706 at least one-and-a-quarter full circles. In at least some embodiments, the second loop 804 tapers proximally (see e.g., FIGS. 7A-7B).

The second loop 804 can be formed to any suitable diameter for facilitating stabilization of at least one of the orientation or the position of the mapping catheter 302 when the mapping catheter 302 is inserted into patient vasculature. In at least some embodiments, the second loop 804 has a diameter that is smaller in length than the first loop 802.

In at least some embodiments, the reduced-dimension portion 706 is configured and arranged to preferentially bend when the first loop 802 is held in a fixed position (such as being extended around inner walls of a patient blood vessel) and a force is applied distally approximately along a longitudinal axis of the proximal portion 704 of the mapping catheter 302, as shown by directional arrow 820. In at least some embodiments, when such a force is applied, the reduced-dimension portion 706 is configured and arranged to preferentially bend to advance the proximal portion 404 distally. In at least some embodiments, when such a force is applied, the reduced-dimension portion 706 is configured and arranged to preferentially bend such that the reduced-dimension portion 706 (i.e., the second loop 804) advances distally through the first loop 802. In at least some embodiments, when such a force is applied, the reduced-dimension portion 706 (i.e., the second loop 804) is configured and arranged to preferentially bend such that the section 708 of the mapping catheter 302 proximally adjacent to the reduced-dimension portion 706 advances distally through the first loop 802. In at least some embodiments, the amount of force applied to bend the reduced-dimension portion 806 can be less than the amount of force to bend the remaining portions of the mapping catheter 302.

Figure 8C:
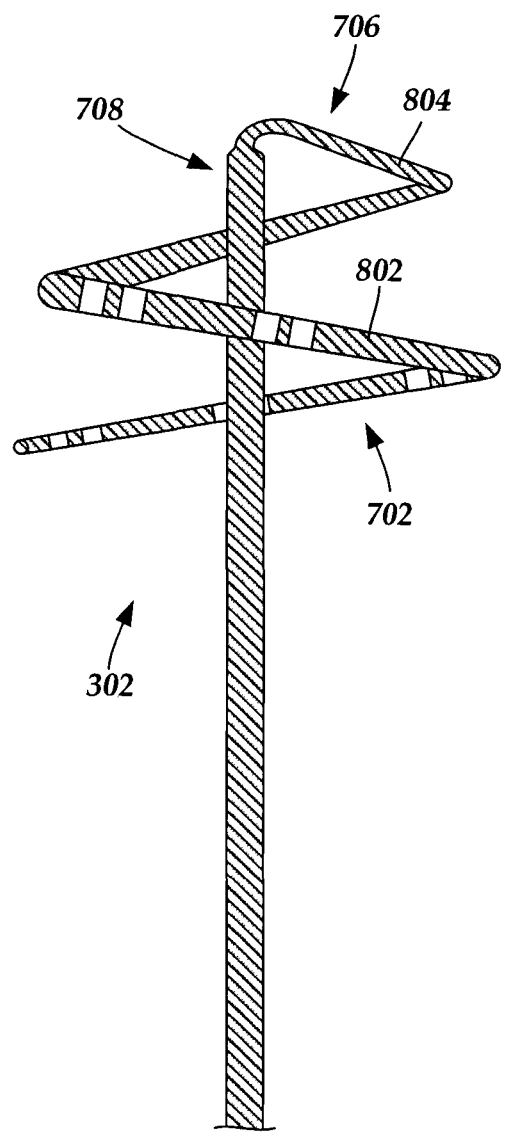
FIG. 8C is a schematic side view of one embodiment of the distal end of the mapping catheter of FIG. 7A disposed in the looped configuration of FIG. 8A and bent along a reduced-dimension portion of the mapping catheter such that the reduced-dimension portion is advanced distally through a first loop formed by a distal portion, according to the invention.

FIG. 8C is a schematic side view of one embodiment of the distal end of the mapping catheter 302. The reduced-dimension portion 706 is bent such that the reduced-dimension portion 706 and the section 708 of the mapping catheter 302 proximally adjacent to the reduced-dimension portion 706 extend through the first loop 802. As shown in FIG. 8C, in at least some embodiments the reduced-dimension portion 706 tapers in a proximal direction. In at least some embodiments, the tapering of the reduced-dimension portion 706 allows for further control of the preferential bending of the reduced-dimension portion 706 by varying the length of at least one transverse dimension along the reduced-dimension portion 706. For example, in at least some embodiments, when the reduced-dimension portion 706 tapers in a proximal direction, a proximal end of the reduced-dimension portion 706 bends preferentially to a distal end of the reduced-dimension portion 706.

The mapping catheter 302 can be positioned to abut patient tissue to be electrically mapped. The distal end of the mapping catheter 302 can be extended from the ablation catheter 102. Once extended from the ablation catheter 102, the distal portion 702 can bend to form the first loop 802 and the reduced-dimension portion 706 can bend to form a second loop 804 disposed proximal to the first loop 802. The mapping catheter 302 can be positioned against patient tissue such that the electrodes 306 (disposed at least in part on the first loop 802) contact patient tissue at the site to be mapped.

Figure 9A:
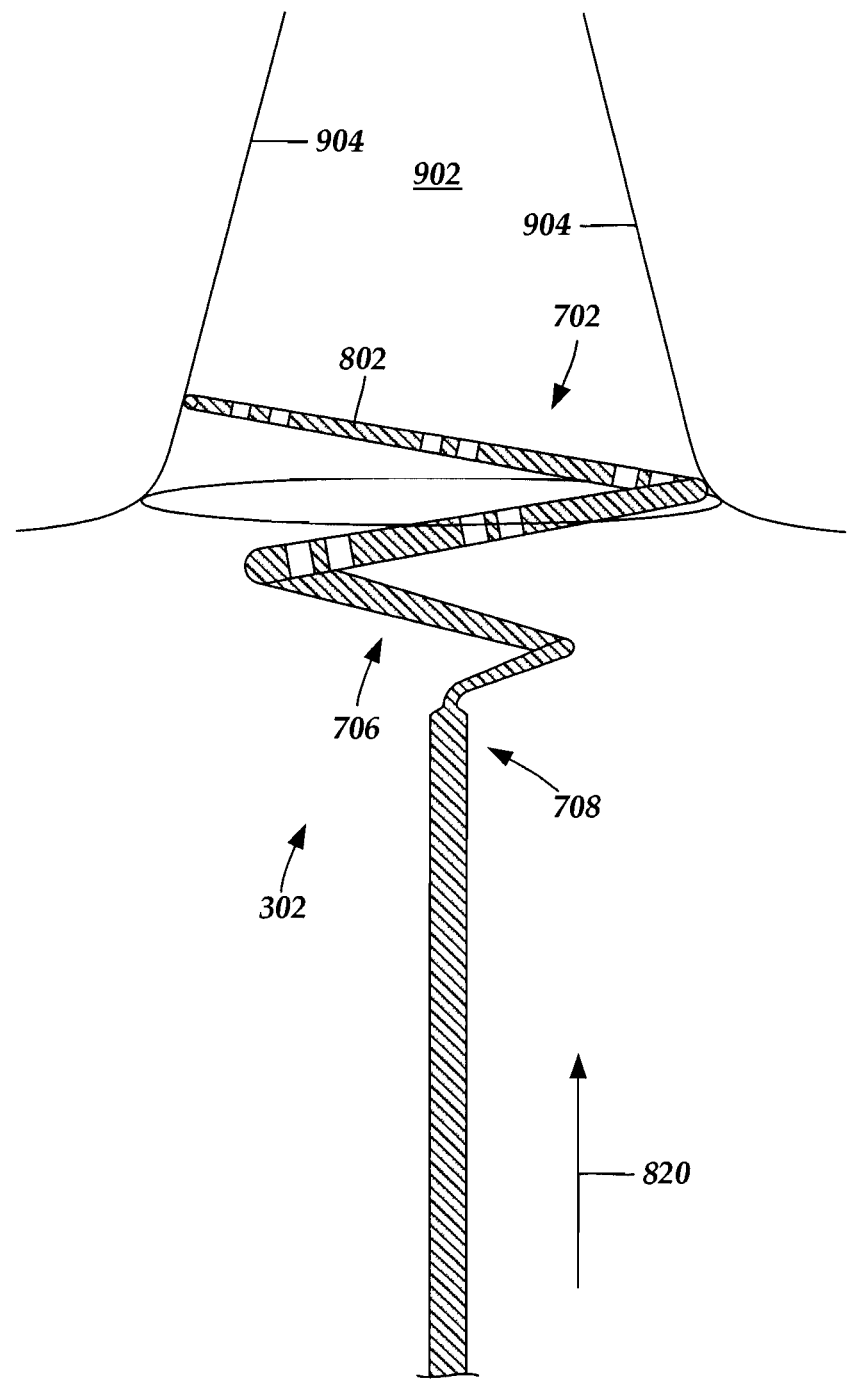
FIG. 9A is a schematic side view of one embodiment of the mapping catheter of FIG. 7A disposed in the looped configuration of FIG. 8B and disposed in an ostium of a pulmonary vein such that a first loop formed by a distal portion of the mapping catheter abuts patient tissue in proximity to the ostium, according to the invention.
Figure 9B:
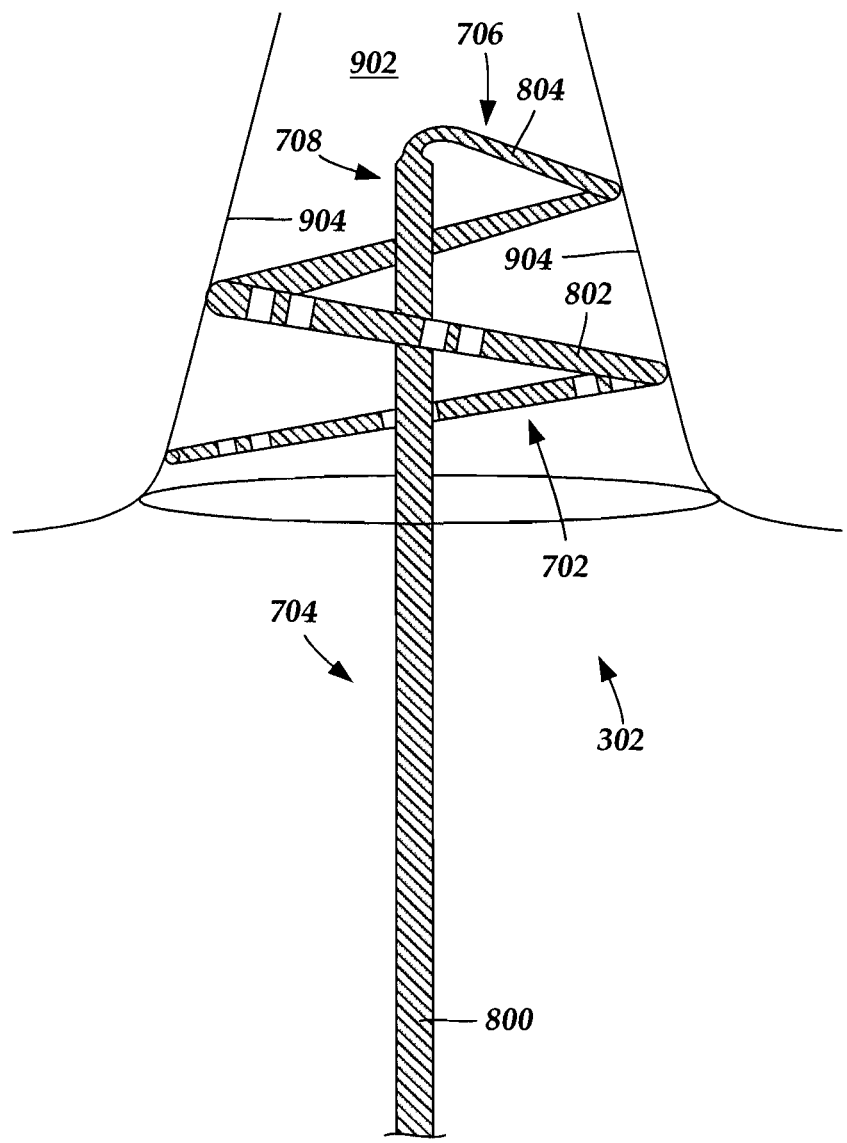
FIG. 9B is a schematic side view of one embodiment of the mapping catheter of FIG. 9A disposed in an ostium of a pulmonary vein, the mapping catheter bent along a reduced-dimension portion of the mapping catheter such that the reduced-dimension is advanced distally through a first loop formed by the distal portion, according to the invention.

FIG. 9A is a schematic side view of one embodiment of the mapping catheter 302 formed into a looped configuration and disposed in an ostium 902 of a pulmonary vein such that the first loop 802 of the mapping catheter 302 abuts patient tissue along inner walls 904 of the ostium 902. In FIGS. 9A-9B the walls 904 are shown as being transparent for clarity of illustration. A force may be applied to the mapping catheter 302 in the direction indicated by directional arrow 820. The force causes the reduced-dimension portion 706 (i.e., the second loop 804) of the mapping catheter 302 to preferentially bend such that the reduced-dimension portion 706 of the mapping catheter 302 advances distally through the first loop 802. In at least some embodiments, the force causes the reduced-dimension portion 706 of the mapping catheter 302 to preferentially bend such that the section 708 of the mapping catheter 302 proximally adjacent to the reduced-dimension portion 706 advances distally through the first loop 802.

FIG. 9B is a schematic side view of one embodiment of the mapping catheter 302 disposed in the ostium 902 of a pulmonary vein such that the first loop 802 of the mapping catheter 302 abuts patient tissue 904 in proximity to the ostium 902. The reduced-dimension portion 706 (i.e., the second loop 804) of the mapping catheter 302 is bent such that the reduced-dimension portion 706 of the mapping catheter 302 extends through the first loop 802. In at least some embodiments, the reduced-dimension portion 706 is bent such that the section 708 of the mapping catheter 302 proximally adjacent to the reduced-dimension portion 706 extends through the first loop 802.

In at least some embodiments, when the reduced-dimension portion 706 extends through the first loop 802, the second loop 804 abuts the inner walls 904 of the ostium 902, causing the mapping catheter 302 to anchor more stably within the ostium 902. In at least some embodiments, when the reduced-dimension portion 706 (i.e., the second loop 804) extends distally through the loop 802, the ability of the mapping catheter 302 to tilt, pivot, rock, or shift position within the ostium 902 is reduced from when the reduced-dimension portion 706 is positioned proximal to the loop 802.

Figure 10:
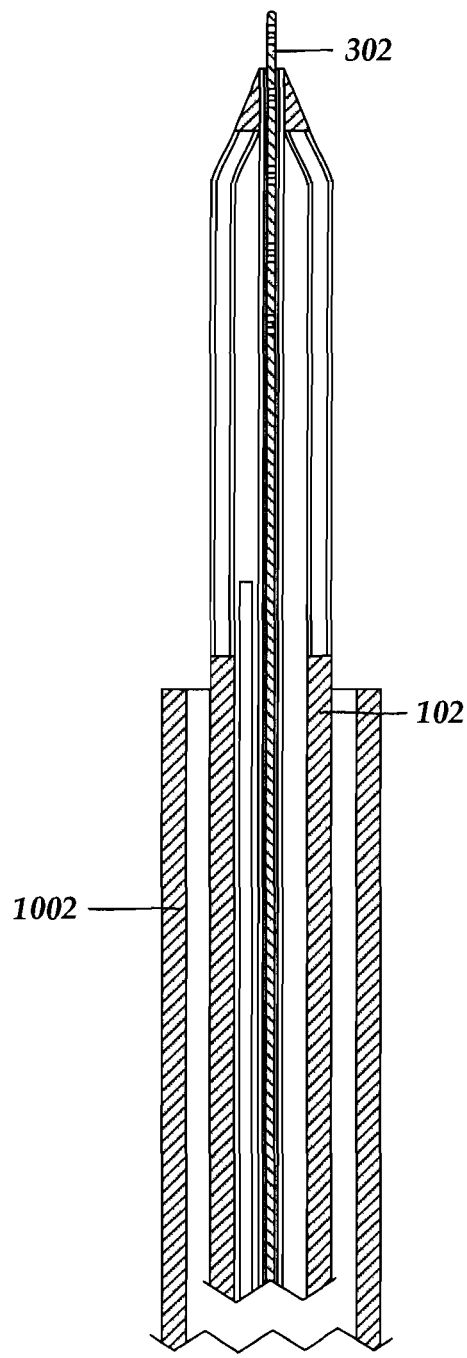
FIG. 10 is a schematic side view of one embodiment of the mapping catheter of FIG. 3 disposed in an ablation catheter which, in turn, is disposed in a sheath, according to the invention.

In at least some embodiments, a sheath may be used to facilitate guidance of the ablation catheter (and mapping catheter) through patient vasculature during insertion of the ablation catheter (and mapping catheter) into a patient. FIG. 10 is a schematic longitudinal cross-sectional view of one embodiment of the distal portion 104 of the ablation catheter 102 disposed in a sheath 1002. In at least some embodiments, the sheath 1002 is steerable. Once the ablation catheter 102 is positioned at a target location, such as the ostia of the pulmonary veins in the left atrium of the heart of the patient, the sheath 1002 can be removed and the mapping catheter 302 can be extended from the ablation catheter 102.

The above specification, examples and data provide a description of the manufacture and use of the composition of the invention. Since many embodiments of the invention can be made without departing from the spirit and scope of the invention, the invention also resides in the claims hereinafter appended.

What is claimed is:

1. A mapping catheter comprising:
   an elongated body configured and arranged for insertion into patient vasculature, wherein a distal end of the elongated body comprises:
      a distal portion comprising a plurality of electrodes;
      a proximal portion disposed proximal to the distal portion; and
      a reduced-dimension portion disposed between the proximal portion and the distal portion, the reduced-dimension portion having a transverse cross-sectional shape that is rectangular and a cross-sectional dimension that is less than corresponding cross-sectional dimensions of the proximal and distal portions adjacent the reduced-dimension portion;
   wherein the distal end is formed, at least in part, from a memory shape material that bends into a preformed shape upon release from a confined space, the preformed shape comprising a first loop formed, at least in part, by the distal portion, wherein the first loop is transverse to a longitudinal axis of the proximal portion,
   wherein the reduced-dimension portion is configured and arranged to bend such that the reduced-dimension portion advances distally through the first loop when the first loop is held in a fixed position and a force is applied along the longitudinal axis of the proximal portion in a distal direction.

2. The mapping catheter of claim 1, wherein the reduced-dimension portion comprises a first dimension and a second dimension that is perpendicular to the first dimension and that is no larger than the first dimension.

3. The mapping catheter of claim 2, wherein the first dimension of the reduced-dimension portion is no more than ten times larger than the second dimension.

4. The mapping catheter of claim 2, wherein the second dimension of the reduced-dimension portion is smaller than a largest transverse cross-sectional dimension of the distal portion.

5. The mapping catheter of claim 1, wherein the distal portion has a transverse cross-sectional shape that is round.

6. The mapping catheter of claim 1, wherein the proximal portion has a transverse cross-sectional shape that is round.

7. The mapping catheter of claim 1, wherein the distal portion of the mapping catheter tapers in a distal direction.

8. The mapping catheter of claim 1, wherein the reduced-dimension portion of the mapping catheter tapers in a proximal direction.

9. The mapping catheter of claim 1, wherein the reduced-dimension portion is configured and arranged to bend preferentially in a dimension such that a distal end of the proximal portion advances distally through the first loop when the first loop is held in a fixed position and a force is applied along the axis of the proximal portion in a distal direction.

10. The mapping catheter of claim 1, wherein the preformed shape comprises a second loop formed, at least in part, by the reduced-dimension portion.

11. The mapping catheter of claim 10, wherein the first loop and the second loop are parallel.

12. The mapping catheter of claim 10, wherein the first loop has a transverse diameter that is larger than a transverse diameter of the second loop.

13. An ablation system comprising:
   an ablation catheter having a distal portion, a proximal portion, and a longitudinal length, the ablation catheter configured and arranged for insertion into patient vasculature;
   an expansion element coupled to the distal portion of the ablation catheter, the expansion element configured and arranged for ablating patient tissue;
   a mapping catheter comprising an elongated body insertable into the ablation catheter, the elongated body comprising a distal end that is extendable from a distal end of the ablation catheter, the distal end of the elongated body comprising:
      a distal portion comprising a plurality of electrodes,
      a proximal portion disposed proximal to the distal portion, and
      a reduced-dimension portion disposed between the proximal portion and the distal portion, the reduced-dimension portion having a transverse cross-sectional shape that is rectangular and a cross-sectional dimension that is less than corresponding cross-sectional dimensions of the proximal and distal portions adjacent the reduced-dimension portion;
   wherein the distal end is formed, at least in part, from a memory shape material that bends into a preformed shape upon release from a confined space, the preformed shape comprising a first loop formed, at least in part, by the distal portion,
   wherein the first loop is transverse to a longitudinal axis of the proximal portion, wherein the reduced-dimension portion is configured and arranged to bend such that the reduced-dimension portion advances distally through the first loop when the first loop is held in a fixed position and a force is applied along the longitudinal axis of the proximal portion in a distal direction; and a control module coupled to the ablation catheter and the mapping catheter, the control module configured and arranged for controlling the mapping of electrical activity of the mapping catheter and the ablation of patient tissue by the ablation catheter.

14. The ablation system of claim 13, wherein the ablation system is a radio frequency ablation system.

15. The ablation system of claim 13, wherein the reduced-dimension portion comprises a first dimension and a second dimension that is perpendicular to the first dimension, wherein the first dimension of the reduced-dimension portion is no more than ten times larger than the second dimension.

16. The ablation system of claim 13, wherein the reduced-dimension portion comprises a first dimension and a second dimension that is perpendicular to the first dimension, wherein the second dimension of the reduced-dimension portion is smaller than a largest transverse cross-sectional dimension of the distal portion.

17. The ablation system of claim 13, wherein the distal portion and the proximal portion both have a transverse cross-sectional shape that is round.

18. The ablation system of claim 13, wherein the reduced-dimension portion is configured and arranged to bend preferentially such that a distal end of the proximal portion advances distally through the first loop when the first loop is held in a fixed position and a force is applied along the axis of the proximal portion in a distal direction.

19. The ablation system of claim 13, wherein the preformed shape comprises a second loop formed, at least in part, by the reduced-dimension portion.

20. The ablation system of claim 19, wherein the first loop has a transverse diameter that is larger than a transverse diameter of the second loop.

* * * * *